US012751991B2

(12) United States Patent
Ruoslahti et al.

(10) Patent No.: US 12,751,991 B2
(45) Date of Patent: Oct. 6, 2026

(54) METHODS FOR TREATING PANCREATIC CANCER AND OTHER SOLID TUMORS

(71) Applicant: LISATA THERAPEUTICS, INC., Basking Ridge, NJ (US)

(72) Inventors: Erkki Ruoslahti, La Jolla, CA (US); Harri Jarvelainen, La Jolla, CA (US)

(73) Assignee: LISATA THERAPEUTICS, INC, Basking Ridge, NJ (US)

( * ) Notice: Subject to any disclaimer, the term of this patent is extended or adjusted under 35 U.S.C. 154(b) by 939 days.

(21) Appl. No.: 17/923,408

(22) PCT Filed: May 4, 2021

(86) PCT No.: PCT/US2021/030740

§ 371 (c)(1),
(2) Date: Nov. 4, 2022

(87) PCT Pub. No.: WO2021/226148

PCT Pub. Date: Nov. 11, 2021

(65) Prior Publication Data

US 2023/0201303 A1 Jun. 29, 2023

Related U.S. Application Data

(60) Provisional application No. 63/019,799, filed on May 4, 2020.

(51) Int. Cl.

| | |
|---|---|
| ***A61K 38/17*** | (2006.01) |
| ***A61K 9/00*** | (2006.01) |
| ***A61K 31/337*** | (2006.01) |
| ***A61K 31/7068*** | (2006.01) |
| ***A61K 35/15*** | (2025.01) |
| ***A61K 35/17*** | (2025.01) |
| ***A61P 35/00*** | (2006.01) |

(52) U.S. Cl.
CPC ........ *A61K 38/1709* (2013.01); *A61K 9/0019* (2013.01); *A61K 31/337* (2013.01); *A61K 31/7068* (2013.01); *A61K 35/15* (2013.01); *A61K 35/17* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 8,367,621 | B2 | 2/2013 | Ruoslahti et al. | |
| 9,073,974 | B2 | 7/2015 | Lam et al. | |
| 9,115,170 | B2 | 8/2015 | Ruoslahti et al. | |
| 9,694,074 | B2 | 7/2017 | Cunin et al. | |
| 10,370,245 | B2 * | 8/2019 | Ruoslahti ................ | A61P 19/02 |
| 11,059,718 | B2 | 7/2021 | Ruoslahti et al. | |
| 11,260,133 | B2 | 3/2022 | Ruoslahti et al. | |
| 2009/0246133 | A1 | 10/2009 | Ruoslahti et al. | |
| 2010/0322862 | A1 * | 12/2010 | Ruoslahti ............... | A61K 47/66 424/9.1 |
| 2013/0115628 | A1 | 5/2013 | Isaacson et al. | |
| 2015/0174263 | A1 * | 6/2015 | Sengupta ............... | A61K 47/55 540/113 |
| 2015/0259380 | A1 | 9/2015 | Ruoslahti et al. | |
| 2017/0216402 | A1 | 8/2017 | Wittrup et al. | |
| 2018/0064662 | A1 | 3/2018 | Fukumura et al. | |
| 2020/0282013 | A1 | 9/2020 | Jarvelainen et al. | |
| 2022/0175941 | A1 | 6/2022 | Ruoslahti et al. | |
| 2023/0201303 | A1 | 6/2023 | Ruoslahti et al. | |

FOREIGN PATENT DOCUMENTS

| | | | |
|---|---|---|---|
| CN | 102600489 | A | 7/2012 |
| CN | 107892710 | A | 4/2018 |
| EP | 2445536 | B1 | 6/2016 |
| JP | 2014226079 | A | 12/2014 |
| JP | 2019501198 | A | 1/2019 |
| WO | 0103718 | A3 | 7/2001 |
| WO | 2012123381 | A1 | 9/2012 |
| WO | 2017120537 | A1 | 7/2017 |
| WO | 2017190684 | A1 | 11/2017 |
| WO | 2018089669 | A2 | 5/2018 |
| WO | 2018213631 | A1 | 11/2018 |

OTHER PUBLICATIONS

Hopkins Medicine (downloaded from URL :<https://www.hopkinsmedicine.org/health/conditions-and-diseases/pancreatic-cancer/pancreatic-cancer-types>) (Year: 2025).*

Hurtado De Mendoza et al. "Tumor-penetrating therapy for 5 integrin-rich pancreas cancer," Nature Communications. Mar. 9, 2021 (Mar. 9, 2021), vol. 12, No. 1541. pp. 1-13. entire document.

PCT/IB/326 Form: International Preliminary Report on Patentability for PCT/US2021/030740 dated Nov. 17, 2022.

CEND-1 in Combination With Nabpaclitaxel and Gemcitabine in Metastatic Pancreatic Cancer, NCT03517176 (ver. 11), ClinicalTrials.gov [online], Dec. 4, 2019, [date of retrieval: Oct. 24, 2025].

Akashi; Anticancer Effects of Gemcitabine are Enhanced by co-administered iRGD peptide in murine pancreatic cancer models that overespressed neuropilin-a; British Journal of Cancer, 2014- 110, 1481-1487- 7 pages.

Alva et al., Cancer Immunol Immunother. 2016; 65(12): 1533-1544).

Botta et al., "iRGD in Combination with IL-2 Reprograms Tumor Immunosuppression" NIH KL2TR002552, NCI KYGF9753, SCMG Grant 90105000008254, SBP Grant 04032018; SBP Medical Discovery Institute, 1 page.

Botta et al.; iRGD in combination with IL-2 reprograms tumor immunosuppression; Journal of Clinical Oncology; 2019, 3 pages.

Botta et al.; Digital Program: 2019 ASCO-SITC Clinical Immuno-Oncology Symposium; Feb. 28-Mar. 2, 2019; ASCO Meeting Library, 3 pages.

Cayrol et al. The IL-1-like cytokine I L-33 is inactivated after maturation by caspase-1. Proc Natl Acad Sci U SA. Jun. 2, 2009; 106(22 ): 9021-9026. (Year: 2009).

Charych et al (2016). NKTR-214, an Engineered Cytokine with Biased IL2 Receptor Binding, Increased Tumor Exposure, and Marked Efficacy in Mouse Tumor Models. Clin Cancer Res 22: 680-690.

(Continued)

*Primary Examiner* — Sergio Coffa
(74) *Attorney, Agent, or Firm* — PROCOPIO, CORY, HARGREAVES & SAVITCH LLP

(57) ABSTRACT

Provided herein are methods and compositions for treating solid tumor cancers.

14 Claims, 2 Drawing Sheets

(56) References Cited

OTHER PUBLICATIONS

Dean et al. 1528P Phase I trial of the first-in-class agent CEND-1 in combination with gemcitabine and nab-paclitaxel in patients with metastatic pancreatic cancer. Annals of Oncology. 2020;31 (4):S 934) (Year: 2020).
Dean et al. (Lancet Gastroenterol Hepatol 2022; 7: 943-51) (Year: 2022).
Dutcher, J. P. et al., High dose interleukin-2 (Aldesleukin)—expert consensus of best management practices-2014, Journal for Immunotherapy of Cancer, 2014, vol. 2, No. 1, 26, doi: 10.1186/s40425-014-0026-0.
Harada, K. et al., Long-term response to very-low-dose interleukin-2 therapy in patients with metastatic renal cell carcinoma; report of two cases, Clinical and Experimental Nephrology, 2011, vol. 15, No. 6, pp. 966 to 968, doi:10.1007/s10157-011-0518-x (newly cited publication).
ISR related to PCT/US2020/21570 dated Jun. 22, 2020.
Jarvelainen, H et al. Abstract 1 106: co-administration of the IRGD tumorpenetrating peptide.
Johnson et al. Nature Communications 17:10582, Melanoma-specific MHC-11 expression represents a tumour-autonomous phenotype and predicts response to anti-PD-1/PD-L 1 therapy (Year: 2015).
Liu et al. (Mol Syst Des Eng. Oct. 1, 2017; 2(4): 370-379) (Year: 2017).
Medical news today by Christina Chun, https://www.medicalnewstoday.com/articles/322700 Accessed May 8, 2020 (Year: 2018).
"Merck manual, cancer treatment principles, by Robert Gale, https://www.merckmanuals.com/home/cancer/prevention-and-treatment-of-cancer/cancer-treatment-pri nci ples?query=Cancer%2otreatment Accessed May 8, 2020 (Year: 2018) ".
Merck manual, overview of cancer therapy, by Robert Gale, https://www.merckmanuals.com/professional/hematology-and-oncology /principles-of-cancer-therapy/overview-of-cancer-therapy?query= Cancer Accessed May 8, 2020 (Year: 2018).
National cancer institute, what is cancer? https://www.cancer.gov/about-cancer/understanding/what-is-cancer accessed on May 8, 2020 (Year: 2015).
National cancer institute, cancer prevention, https://www.cancer.gov/about-cancer/causes-prevention/ patient-prevention-overview-pdq accessed May 8, 2020 (Year: 2020).
Pan et al. (Cell Rep Med. Jun. 18, 2024;5(6):101590) (Year: 2024).
PCT/IB/326 Form: International Preliminary Report on Patentability for PCT/US2021/03074.
Rosenberg; "Raising the Bar: The Curative Potential of Human Cancer Immunotherapy", Sci Transl Med. Mar. 28, 2012; 4(127): 127ps8. doi:10.1126/scitranslmed.3003634.
Rosenzwajg et al., "Low dose interleukin-2 fosters a dose-dependent regulatory T cell tuned milieu in T1 D patients" J Autoimmun., Apr. 2015; 58:48-58.
Ruoslahti (2017). Tumor penetrating peptides for improved drug delivery. Adv Drug Deliv Rev. 110-111: 3-12.
Sausville et al. Contributions of Human Tumor Xenografts to Anticancer Drug Development. Cancer Res 2006; 66: (7). Apr. 1, 2006 (Year: 2006).
Schmithals et al., Improving Drug Penetrability with iRGD Leverages the Therapeutic Response to Sorafenib nd Doxorubicin in Hepatocellular Carcinoma, Cancer Research- Therapeutics, Targets and Chemical Biology, 2015, pp. 3147-3154.
Sugahara et al. Co-administration of a Tumor-Penetrating Peptide Enhances the Efficacy of Cancer Drugs. Science. May 21, 2010; 328(5981): 1031-1035 (Year: 2010).
Waldmann (2015). The shared and contrasting roles of interleukin-2 (IL-2) and IL-15 in the life and death of normal and neoplastic lymphocytes: implications for cancer therapy. Cancer Immunol Res. 3: 219-227.
Walker et al., Using protein-based motifs to stabilize peptides, J. Peptide Res., 2003, 62, 214-226.
Yang Jie et al: "Modification of IL-24 by 1-6,8-14 tumor penetrating peptide iRGD enhanced its antitumor efficacy Feb. 22, 2019), pp. 125-134, XP085646038_ 3 ligainst non-small cell lung cancer", International Immunopharmacology, vol. 70, Feb. 22, 2019.
Zeng et al. N-Terminal Acetylation and C-Terminal Amidation of Spirulina platensis-Derived Hexapeptide: Anti-Photoaging Activity and Proteomic Analysis. Mar. Drugs. 2019, 17, 520. (Year: 2019).
Zhong et al., Co-Administered or iRGD Enhances Tumor-Targeted Delivery and Anti-Tumor Effects of Paclitaxel-Loaded PLGA Nanoparticles For Colorectal Cancer Treatment , International Journal of Nanomedicine; 18 pages,2019.
CEND-1 Injection (QLC12102) in Patients With Advanced Metastatic Pancreatic Ductal Adenocarcinoma; ClinicalTrials.gov ID NCT05052567, Sponsor Qilu Pharmaceutical Co., Ltd., Last Update Posted Sep. 4, 2024; https://clinicaltrials.gov/study/NCT05052567?term=CEND-1&rank=1.
CEND-1 in Combination With Nabpaclitaxel and Gemcitabine in Metastatic Pancreatic Cancer, ClinicalTrials.gov ID NCT03517176, Sponsor Lisata Therapeutics, Inc., Information provided by Lisata Therapeutics, Inc. (Responsible Party) , Last Update Posted Aug. 28, 2024, https://clinicaltrials.gov/study/NCT03517176?term=CEND-1&rank=2.
A Study of CEND-1 With Chemotherapy as First-Line Therapy in Patients With Pancreatic Ductal Adenocarcinoma, ClinicalTrials.gov ID NCT06261359, Sponsor Qilu Pharmaceutical Co., Ltd., Information provided by Qilu Pharmaceutical Co., Ltd. (Responsible Party) , Last Update Posted Sep. 4, 2024, https://clinicaltrials.gov/study/NCT06261359?term=CEND-1&rank=3.
CEND-1 in Combination with Neoadjuvant FOLFIRINOX with or Without Panitumumab (CENDIFOX), ClinicalTrials.gov ID NCT05121038, Sponsor Anup Kasi, Information provided by Anup Kasi, University of Kansas Medical Center (Responsible Party) , Last Update Posted Dec. 17, 2024, https://clinicaltrials.gov/study/NCT05121038?term=CEND-1&rank=4.
LSTA1 Phase 1b/□2a Continuous Infusion Trial in mPDAC (FORTIFIDE), ClinicalTrials.gov ID NCT06592664, Sponsor Lisata Therapeutics, Inc., Information provided by Lisata Therapeutics, Inc. (Responsible Party) , Last Update Posted Dec. 13, 2024, https://clinicaltrials.gov/study/NCT06592664?term=CEND-1&rank=5.
The ASCEND Study: Gemcitabine and Nab-Paclitaxel With LSTA1 (Certepetide) or Placebo in Patients With Untreated Metastatic Pancreatic Ductal Adenocarcinoma (ASCEND), ClinicalTrials.gov ID NCT05042128, Sponsor Australasian Gastro-Intestinal Trials Group, Information provided by Australasian Gastro-Intestinal Trials Group (Responsible Party) , Last Update Posted Oct. 22, 2024, https://clinicaltrials.gov/study/NCT05042128?term=CEND-1&rank=6.
A Study of LSTA1 When Added to Standard of Care Versus Standard of Care Alone in Patients With Advanced Solid Tumors (BOLSTER), ClinicalTrials. gov ID NCT05712356, Sponsor Lisata Therapeutics, Inc., Information provided by Lisata Therapeutics, Inc. (Responsible Party) , Last Update Posted Mar. 14, 2025, https://clinicaltrials.gov/study/NCT05712356?term=CEND-1&rank=7.

* cited by examiner

METHODS FOR TREATING PANCREATIC CANCER AND OTHER SOLID TUMORS

CROSS-REFERENCE TO RELATED APPLICATIONS

This application is a U.S. National Stage entry of PCT Application No. PCT/US21/30740, filed May 4, 2021, which claims priority to U.S. Provisional Application No. 63/019,799, filed on May 4, 2020, all the contents of which are incorporated herein by reference.

The invention relates to methods and medicaments useful for treating solid tumors, e.g., pancreatic adenocarcinoma and other solid tumors with a combination of CEND-1 peptide and anti-cancer therapies, e.g., standard-of-care anti-cancer therapies.

BACKGROUND

The National Cancer Institute estimates that in 2018 approximately 1,735,350 new cases of cancer will be diagnosed in the United States and 609,640 people will die from the disease. Despite advances in the treatment of certain forms of cancer through surgery, radiotherapy, chemotherapy, and most recently immunotherapy, most types of solid tumors are essentially incurable. Even when an effective treatment is available for a particular cancer, the side effects from the treatment can have a significant adverse impact on a patient's quality of life.

Pancreatic cancer is an especially serious cancer and a life-threatening condition. In most cases, early stages of the disease are asymptomatic and less than 20% of pancreatic cancers are amenable to surgery. Moreover, invasive and metastatic pancreatic cancers respond poorly to existing treatments in chemotherapy and radiotherapy, with response rates typically less than 30%. The National Cancer Institute (NCI) estimate that survival rate for cancer of the exocrine pancreas is less than 5% and the median survival time after diagnosis is less than a year. The continuing poor prognosis and lack of effective treatments for pancreatic cancer highlight an unmet medical need to develop less toxic and more efficient treatment strategies that improve the clinical management and prognosis of patients afflicted with pancreatic cancer.

An important reason for why most anti-cancer agents have toxicity and limited efficacy for solid tumors is the fact that anti-cancer drugs only penetrate 3-5 cell diameters deep from the blood vessels, leaving some areas of the tumor exposed to an ineffective concentration of the drug or to no drug at all. As an example, studies have suggested that less than 1% of the administered nabpaclitaxel may be able to penetrate/enter the pancreatic ductal adenocarcinoma tissue.

SUMMARY

Improved Penetration of Chemotherapeutics with CEND-1

The results from both in vivo and in vitro pharmacology and mechanistic studies indicate that combining the invention CEND-1/iRGD-analog (FIG. 2) with chemotherapeutics significantly increases the tumor penetration of these drugs and improves their efficacy. Although the invention methods are applicable to a broad class of cancers and/or solid tumors, the initial indication for this investigational drug is pancreatic ductal adenocarcinoma (PDAC) because, in addition to its poor prognosis, it is characterized by a dense extracellular matrix stroma, which acts as a physical barrier to drug entry. Since the tumor homing and the transport process initiated by CEND-1 have been shown to be active in the PDAC stroma and preclinical studies have shown increased drug penetration and efficacy in different kinds of PDAC models, CEND-1 appears particularly well suited to target PDAC.

Provided herein are methods for treating, inhibiting, or reducing the volume of a tumor of a cancer in a subject or patient in need thereof, wherein the method comprises administering CEND-1, or a pharmaceutically acceptable salt thereof, in a combination with simultaneous, separate or sequential administration of at least one anti-cancer agent or therapy. In certain embodiments, the tumor is a malignant solid tumor characterized by dense tumor stroma. In other embodiments, the tumor is a solid tumor of a cancer selected from the group consisting of: breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma, and head and neck cancer. In another embodiment, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (such as Stage 0-IV, and the like.

In particular embodiments, the anti-cancer agent or therapy is selected from the group consisting of: a chemotherapeutic agent, small molecule, antibody, antibody drug conjugate, nanoparticle, cell therapy, polypeptides, peptides, peptidomimetics, nucleic acid-molecules, ribozymes, antisense oligonucleotides, and nucleic acid molecules encoding transgenes, viruses, cytokines, cytotoxic polypeptides; pro-apoptotic polypeptides, anti-angiogenic polypeptides. cytotoxic cells such as cytotoxic T cells, and/or vaccines (mRNA or DNA).

In other embodiments, the chemotherapeutic agent is selected from one or more of the group consisting of: taxane, docetaxel, paclitaxel, nab-paclitaxel, a nucleoside, gemcitabine, an anthracycline, doxorubicin, an alkylating agent, a *vinca* alkaloid, an anti-metabolite, a platinum agent, cisplatin, carboplatin, a steroid, methotrexate, an antibiotic, adriamycin, an isofamide, a selective estrogen receptor modulator, a maytansinoid, mertansine, emtansine, an antibody such, trastuzumab, an anti-epidermal growth factor receptor 2 (HER2) antibody, trastuzumab, a caspase, caspase-8; diphtheria toxin A chain, *Pseudomonas* exotoxin A, cholera toxin, ligand fusion toxins, DAB389EGF, *Ricinus communis* toxin (ricin); chimeric antigen receptor T cells (CAR-T), chimeric antigen receptor macrophages (CAR-M), chimeric antigen receptor natural killer cells (CAR-K), and tumor-infiltrating lymphocytes (TIL), anti-PD-1 antibodies, nivolumab, pembrolizumab, atezolizumab, avelumab, durvalumab; anti-CTLA-4 antibodies. ipilimumab; bispecific antibodies, catumaxomab, Moderna's mRNA-4157 and/or BioNTech's BNT122.

In particular embodiments, the CEND-1 (e.g, the iRGD-analog set forth in FIG. 2) is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In a particular embodiment, CEND-1 is administered in an amount corresponding to 3.2 mg/kg body weight/per dose of cancer therapy.

In certain embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every 10th day, once every 11th day, once every 12th day, once every 13th day, once every 2 weeks, once every 3 weeks, and/or once per month. In one embodiment, CEND-1 is present in a dry formulation or suspended in a biocompatible medium.

In particular embodiments, the biocompatible media is selected from the group consisting of: water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, and lipid-containing emulsions. In a particular embodiment, CEND-1 is administered intravenously.

Also provided herein is a method of treating pancreatic cancer in a patient in need thereof, comprising administering to the patient an effective amount of CEND-1, in combination with gemcitabine and/or nab-paclitaxel, or pharmaceutically acceptable salts thereof. In certain embodiments, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (Stage 0-IV).

In certain embodiments, CEND-1 is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In once embodiment, CEND-1 is administered in an amount corresponding to 3.2 mg/kg body weight/per dose of cancer therapy.

In particular embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every. 10th day, once every 11th day, once every 12th day, once every 13th day, once every 2 weeks, once every 3 weeks, and/or once per month. In a particular embodiment, CEND-1 is administered in a range amount selected from: 0.01-100, 0.02-90, 0.03-80, 0.04-70, 0.05-60, 0.06-50, 0.07-40, 0.08-30, 0.09-30, 0.1-25, 0.11-20, 0.12-15, 0.13-10, 0.14-9, 0.15-8, 0.16-7, 0.17-6, 0.18-5, 0.19-4, or 0.2-3.2 mg/kg body weight/day or per dose of chemotherapy;

nab-paclitaxel is administered in a range amount selected from: 1-500, 10-450, 20-400, 30-350, 40-300, 50-250, 60-200, 70-175, 80-160, 90-150, 100-140, 110-140, 115-135 or 120-130 mg/m2; and gemcitabine is administered in a range amount selected from: 1-5000, 100-4500, 200-4000, 300-3500, 400-3000, 500-2500, 550-2000, 600-1750, 650-1500, 700-1400, 750-1300, 800-1200, or 900-1100 mg/m2.

In yet another embodiment, CEND-1 is administered in a range of 0.2-3.2 mg/kg body weight/day or per dose of chemotherapy; nab-paclitaxel is administered at 125 mg/m2; and gemcitabine is administered at 1000 mg/m2.

In certain embodiments of the invention methods provided herein, efficacy or clinical activity of the method is measured by determining: Overall Response Rate (ORR), Progression Free Survival (PFS) and/or Overall Survival (OS). In yet further embodiments, efficacy or clinical activity of the method is measured by determining one or more of: an Overall Response Rate (ORR) selected from greater than 25%, 30%, 35%, 40%, 45%, 50%, 55%, 60%, 65%, 70%, 75%, 80%, 85%, 90%, or greater that 95%; a Progression Free Survival (PFS) selected from greater than 25%, 30%, 35%, 40%, 45%, 50%, 55%, 60%, 65%, 70%, 75%, 80%, 85%, 90%, or greater that 95%; and/or an Overall Survival (OS) selected from greater than 25%, 30%, 35%, 40%, 45%, 50%, 55%, 60%, 65%, 70%, 75%, 80%, 85%, 90%, or greater that 95%.

Also provided herein are pharmaceutical composition comprising: a CEND-1/iRGD-analog and a pharmaceutically acceptable excipient. In a particular embodiment, the invention composition corresponds to the iRGD-analog is set forth as the structure in FIG. 2 (CEND-1/iRGD-analog). The invention iRGD-analog differs from the prior art iRGD peptides in the specific moieties used to block the amino and carboxy termini, which has resulted in significant advantages over prior art cyclic iRGD peptides. For example, the invention CEND-1/iRGD-analog (set forth in FIG. 2) has the following Molecular formula C37 H60 N14 O14 S2; a MW 989.1; and the recent CAS Registry #: 2580154-08-3. Whereas one prior art iRGD with at least one inferior therapeutic property corresponds to an iRGD having the Molecular Formula: $C_{35}H_{57}N_{13}O_{14}S_2$; a Molecular Weight of 948.04; and CAS Registry No. 1392278-76-0.

Advantages of the invention iRGD-analog (FIG. 2; C37 H60 N14 O14 S2; MW 989.1), relative to prior art CAS Registry No. 1392278-76-0 cyclic peptide and other known iRGD molecules, while maintaining favorable in vitro/in vivo potency and efficacy include one or more of the following:

Favorable pharmacokinetic properties;
Improved stability in plasma/serum;
Improved stability in formulated solution;
Improved stability in storage; and/or
Improved protection from proteases such as aminopeptidases and carboxypeptidases.

In certain embodiments, favorable and/or improved pharmacokinetic properties are selected from one or more of absorption, distribution, metabolism, and/or excretion.

Also provided herein is a kit or composition comprising an iRGD-analog (CEND-1); and an anti-cancer agent. In a particular embodiment, the iRGD-analog is set forth as the structure in FIG. 2.

DETAILED DESCRIPTION

Figure 1:
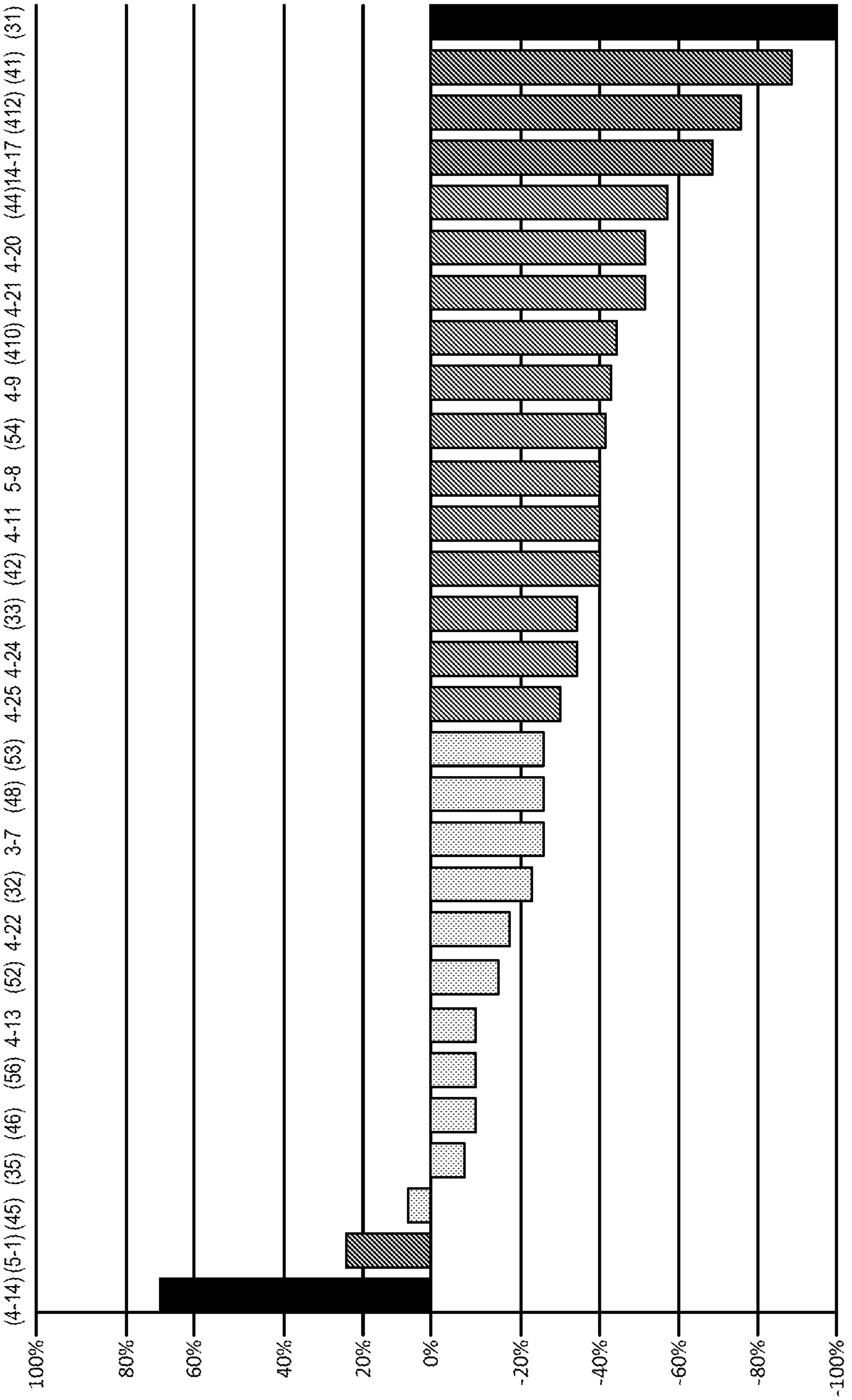
FIG. 1 shows a waterfall plot described in the Examples.

Provided herein are methods for treating, inhibiting, or reducing the volume of a tumor of a cancer in a subject or patient in need thereof, wherein the method comprises administering CEND-1, or a pharmaceutically acceptable salt thereof, in a combination with simultaneous, separate or sequential administration of at least one anti-cancer agent or therapy. The invention provides improved methods and medicaments for more effectively treating solid tumors with anti-cancer therapies. CEND-1 is a tumor-penetrating peptide (also known as iRGD and internalizing arginylglycylaspartic acid cyclic peptide), with a cyclizing (S—S bond through the cysteine side chains) structure containing nine amino acids. In a particular embodiment, an invention CEND-1/iRGD-analog corresponds to the invention iRGD-analog peptide sequence corresponding to the specific cyclic peptide chemical structure set forth in FIG. 2, set forth as Ac-Cys-Arg-Gly-Asp-Lys-Gly-Pro-Asp-Cys-NH2 and having CAS Registry #2580154-02-3. The pharmacological effect of CEND-1 is restricted to tumors via the primary RGD tumor homing motif interaction with αv-integrins (highly expressed in growing tumors but not in healthy tissues). The secondary 'CendR'—motif modulates the tumor microenvironment via NRP-1. Based on experimental models, the interaction with neuropilin-1 leads to transformation of the solid tumor microenvironment into a temporary drug conduit, allowing an efficient tumor access of anti-cancer therapies given in combination with CEND-1. Studies have demonstrated that CEND-1 increases, via the above-mentioned tumor microenvironment modulation mechanism, accumulation and penetration of anticancer drugs into tumors, but not into normal tissues. As a result, anti-tumor activity is enhanced, while the therapeutic margins/safety profile is potentially improved. In addition to the invention CEND-1/iRGD-analog (FIG. 2); other iRGD peptides and anglogs known in the art, such as those described hereinabove, can be used in the invention methods, in view of the data, dosages and results provided herein.

In certain embodiments, the tumor is a malignant solid tumor characterized by dense tumor stroma. In other embodiments, the tumor is a solid tumor of a cancer selected from the group consisting of: breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma, and head and neck cancer. In another embodiment, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (such as Stage 0-IV, and the like.

As used herein the phrase "solid tumor" refers to essentially solid neoplasmic growth, with low liquid content that is other than a cyst or tumor metastasis (i.e. at its metastatic stage of disease).

As used herein, the phrase "in a combination" refers to administering more that one therapeutic agent to a respective patient in need thereof. In particular embodiments, CEND-1 is administered with at least one other anti-cancer therapeutic agent.

As used herein, the phrase "simultaneous, separate or sequential administration" refers to administering CEND-1 at the same time as the one or more other cancer therapeutic agents; or either before or after administration with the co-administered anti-cancer agents; such that the co-administration can be from separate pharmaceutical compositions administered with either the same or different dosing regimens. In certain embodiments, CEND-1 is administered before the subsequent and sequential administration of the one or more anti-cancer agents.

As used herein, the term "malignant" refers to a tumor or cancer in which abnormal cells divide without control and can invade nearby tissues. Malignant cancer cells can also spread to other parts of the body through the blood and lymph systems.

Based on the novel drug conduit mechanism discovered by the present inventors, the methods and medicaments of the present invention are suitable for using CEND-1 (e.g., an iRGD-analog) to enhance the therapeutic effects of any anticancer agent used to treat solid tumors. The methods and medicaments of the present invention can thus contain combinations of CEND-1/iRGD-analog with any anticancer agent used to treat solid tumors, such as at least one of a taxane such as docetaxel or paclitaxel (including nab-paclitaxel), a nucleoside such as gemcitabine, an anthracyclin such as doxorubicin, an alkylating agent, a *vinca* alkaloid, an anti-metabolite, a platinum agent such as cisplatin or carboplatin, a steroid such as methotrexate, an antibiotic such as adriamycin, an isofamide, a selective estrogen receptor modulator, or an antibody such as trastuzumab.

An anticancer agent whose effects can be enhanced by CEND-1 can be an antibody such as a humanized monoclonal antibody. As an example, the anti-epidermal growth factor receptor 2 (HER2) antibody, trastuzumab (Herceptin: Genentech, South San Francisco, Calif.) is a therapeutic agent useful in a conjugate for treating HER2/neu overexpressing breast cancers (White et al., Annu. Rev. Med. 52:125-141 (2001)).

Anticancer agents whose effects can be enhanced by CEND-1 also can be cytotoxic agents, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab, antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coro nado-Heinsohn, Cancer J. Sci. Am. 2:175 (1996). One skilled in the art understands that these and additional cytotoxic agents described herein or known in the art can be combined with CEND-1 in the disclosed methods and medicaments.

In one embodiment, an anticancer agent whose effects can be enhanced by CEND-1 can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. An anticancer agent whose effects can be enhanced by CEND-1 can be an anti-angiogenic agent. As used herein, the term "anti-angiogenic agent' means a molecule that reduces or prevents angiogenesis, which is the growth and development of blood vessels. The combination of CEND-1 with anti-angiogenic agents can be used to treat cancer associated with angiogenesis. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and anti gen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

In particular embodiments, the anti-cancer agent or therapy is selected from the group consisting of: a chemotherapeutic agent, small molecule, antibody, antibody drug conjugate, nanoparticle, cell therapy, polypeptides, peptides, peptidomimetics, nucleic acid-molecules, ribozymes, antisense oligonucleotides, and nucleic acid molecules encoding transgenes, viruses, cytokines, cytotoxic polypeptides; pro-apoptotic polypeptides, anti-angiogenic polypeptides. cytotoxic cells such as cytotoxic T cells, and/or vaccines (mRNA or DNA).

In other embodiments, the chemotherapeutic agent is selected from one or more of the group consisting of: taxane, docetaxel, paclitaxel, nab-paclitaxel, a nucleoside, gemcitabine, an anthracycline, doxorubicin, an alkylating agent, a *vinca* alkaloid, an anti-metabolite, a platinum agent, cisplatin, carboplatin, a steroid, methotrexate, an antibiotic, adriamycin, an isofamide, a selective estrogen receptor modulator, a maytansinoid, mertansine, emtansine, an auristatin, monomethyl auristatin E (MMAE) and F (MMAF), a natural antimitotic drug, an antibody, trastuzumab, an anti-epidermal growth factor receptor 2 (HER2) antibody, trastuzumab, a caspase, caspase-8; diphtheria toxin A chain, *Pseudomonas* exotoxin A, cholera toxin, ligand fusion toxins, DAB389EGF, *Ricinus communis* toxin (ricin); chimeric antigen receptor T cells (CAR-T), chimeric antigen receptor macrophages (CAR-M), chimeric antigen receptor natural killer cells (CAR-K), and tumor-infiltrating lymphocytes (TIL), anti-PD-1 antibodies, nivolumab, pembrolizumab, atezolizumab, avelumab, durvalumab; anti-CTLA-4 antibodies. ipilimumab; bispecific antibodies, catumaxomab, anti-CD47 antibodies, enfortumab, sacituzumab, antibody-drug conjugates. Moderna's mRNA-4157 and/or BioNTech's BNT122.

In particular embodiments, the CEND-1 (e.g, the iRGD-analog set forth in FIG. 2) is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In a particular embodiment, CEND-1 is administered in an amount corresponding to 3.2 mg/kg body weight/per dose of cancer therapy.

As used herein, the phrae "per dose of cancer therapy" refers to the co-administration of CEND-1 with one or more anti-cancer agents, such that each time an anti-cancer therapeutic is administered, CEND-1 is likewise co-administered to facilitate the therapeutics penetration into the tumor. The co-administration per dose of CEND-1 does not need to be exactly simultaneous with the therapeutic agent(s), and CEND-1 can be administered either before or after the administration of the therapeutic agent.

In certain embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every 10th day, once every 11th day, once every 12th day, once every 13th day, once every 2 weeks, once every 3 weeks, and/or once per month. In one embodiment, CEND-1 is present in a dry formulation or suspended in a biocompatible medium.

In particular embodiments, the biocompatible media is selected from the group consisting of: water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, and lipid-containing emulsions. In a particular embodiment, CEND-1 is administered intravenously.

The method of the present invention is particularly suitable for the treatment of pancreatic cancer, which is characterized by a prominent dense tumor stroma, acting as a physical barrier to drug entry. Therefore, advanced pancreatic cancer was chosen as the first clinical indication for CEND-1. As an example of clinical usefulness, we show safety and efficacy results of CEND-1 when given alone or in combination with nab-paclitaxel and gemcitabine, including its ability to enhance tumor response.

Also provided herein is a method of treating pancreatic cancer in a patient in need thereof, comprising administering to the patient an effective amount of CEND-1, in combination with gemcitabine and/or nab-paclitaxel, or pharmaceutically acceptable salts thereof. In certain embodiments, the pancreatic cancer is selected from the group consisting of: primary pancreatic cancer, metastatic pancreatic cancer, refractory pancreatic cancer, cancer drug resistant pancreatic cancer and adenocarcinoma. In a particular embodiment, the cancer is ductal adenocarcinoma (Stage 0-IV).

In another embodiment the afore described CEND-1 for use in the treatment of pancreatic cancer can be administered in combination with at least one additional anti-cancer drug, which preferably is known to be effective against pancreatic cancer, such as gemcitabine. In context of the present invention it was found that using a CEND-1 can enhance the clinical activity of other pancreatic cancer drugs such as gemcitabine and nab-paclitaxel administered by the intravenous route.

In certain embodiments, CEND-1 is administered in an amount selected from the group consisting of: about 0.2 to 20 mg/kg body weight/per dose of cancer therapy, about 0.3 to 17 mg/kg body weight/per dose of cancer therapy, about 0.4 to 14 mg/kg body weight/per dose of cancer therapy, about 0.5 to 11 mg/kg body weight/per dose of cancer therapy, about 0.6 to 8 mg/kg body weight/per dose of cancer therapy, about 0.7 to 5 mg/kg body weight/per dose of cancer therapy, about 0.8 to 3.2 mg/kg body weight/per dose of cancer therapy. In once embodiment, CEND-1 is administered in an amount corresponding to 3.2 mg/kg body weight/per dose of cancer therapy.

In particular embodiments, CEND-1 is administered before or during the administration of anti-cancer therapy, wherein the cancer therapy is at a dosing regimen selected from the group consisting of: 4 times/day, 3 times/day, twice daily, once daily, once every other day, once every 2nd day, once every 3rd day, once every 4th day, once every 5th day, once every 6th day, once weekly, once every 8th day, once every 9th day, once every 10th day, once every 11th day, once every 12th day, once every 13th day, once every 2 weeks, once every 3 weeks, and/or once per month. In a particular embodiment, CEND-1 is administered in a range amount selected from: 0.01-100, 0.02-90, 0.03-80, 0.04-70, 0.05-60, 0.06-50, 0.07-40, 0.08-30, 0.09-30, 0.1-25, 0.11-20, 0.12-15, 0.13-10, 0.14-9, 0.15-8, 0.16-7, 0.17-6, 0.18-5, 0.19-4, or 0.2-3.2 mg/kg body weight/day or per dose of chemotherapy;

nab-paclitaxel is administered in a range amount selected from: 1-500, 10-450, 20-400, 30-350, 40-300, 50-250, 60-200, 70-175, 80-160, 90-150, 100-140, 110-140, 115-135 or 120-130 mg/m2; and gemcitabine is administered in a range amount selected from: 1-5000, 100-4500, 200-4000, 300-3500, 400-3000, 500-2500, 550-2000, 600-1750, 650-1500, 700-1400, 750-1300, 800-1200, or 900-1100 mg/m2.

In yet another embodiment: CEND-1 is administered in a range of 0.2-3.2 mg/kg body weight/day or per dose of chemotherapy; nab-paclitaxel is administered at 125 mg/m2; and gemcitabine is administered at 1000 mg/m2.

In certain embodiments of the invention methods provided herein, efficacy or clinical activity of the method is measured by determining: Overall Response Rate (ORR), Progression Free Survival (PFS) and/or Overall Survival (OS). In yet further embodiments, efficacy or clinical activity of the method is measured by determining one or more of: an Overall Response Rate (ORR) selected from greater than 25%, 30%, 35%, 40%, 45%, 50%, 55%, 60%, 65%, 70%, 75%, 80%, 85%, 90%, or greater that 95%; a Progression Free Survival (PFS) selected from greater than 25%, 30%, 35%, 40%, 45%, 50%, 55%, 60%, 65%, 70%, 75%, 80%, 85%, 90%, or greater that 95%; and/or an Overall Survival (OS) selected from greater than 25%, 30%, 35%, 40%, 45%, 50%, 55%, 60%, 65%, 70%, 75%, 80%, 85%, 90%, or greater that 95%.

Also provided herein are pharmaceutical composition comprising: a CEND-1/iRGD-analog and a pharmaceutically acceptable excipient. Pharmaceutically acceptable excipients are well-known in the art. The CEND-1 compositions can be administered to an individual (such as human) via a bolus injection or an infusion, via various routes, including, for example, intravenous, intra-arterial, intraperitoneal, intrapulmonary, oral and inhalation, subcutaneous. In some embodiments, the composition is administered intravenously.

The formulations can be presented in unit-dose or multi-dose sealed containers, such as ampules and vials, and can be stored in a freeze-dried (lyophilized) condition requiring only the addition of the sterile liquid excipient, for example, saline, for injections, immediately prior to us.

In a particular embodiments, CEND-1 for Injection is a sterile, white, lyophilized powder supplied as 100 mg per vial of active ingredient dose strength for intravenous administration. CEND-1 Injection consists of CEND-1 drug substance with sodium acetate trihydrate and mannitol as excipients.

Figure 2:
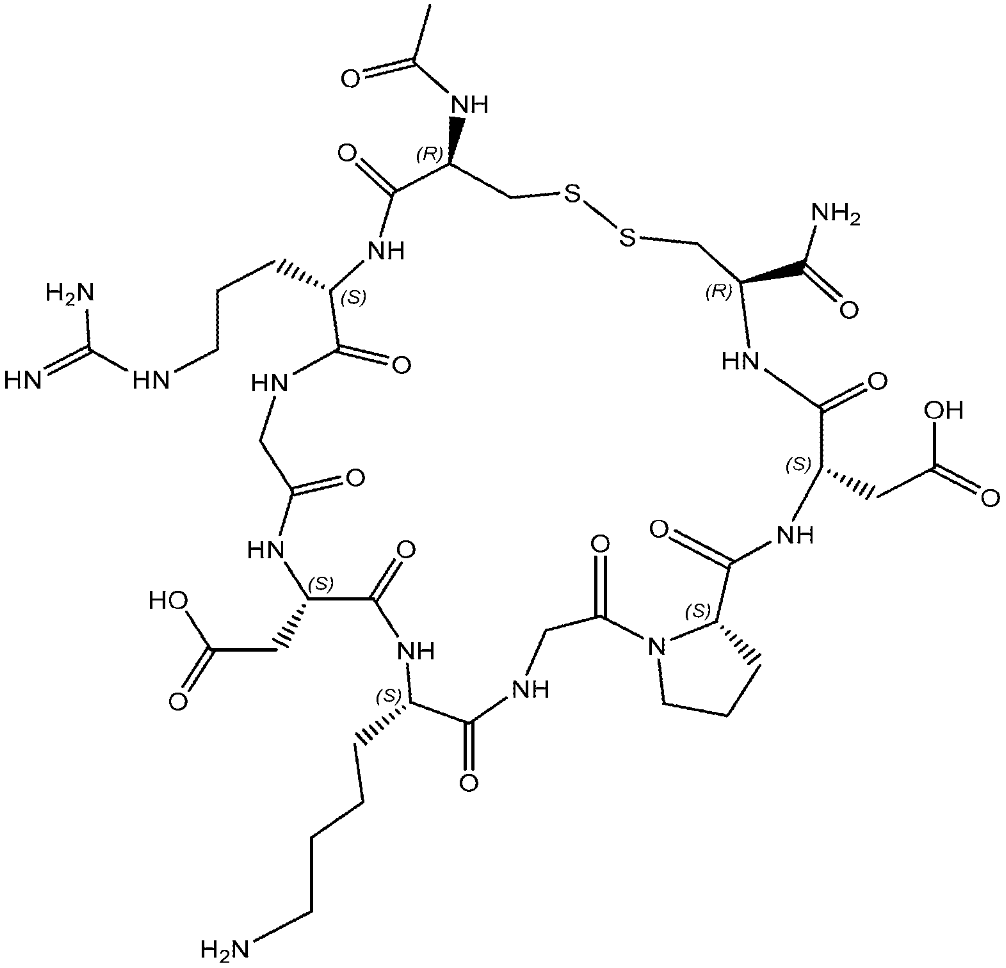
FIG. 2 shows the chemical structure of the invention CEND-1 or CEND-1/iRGD-analog cyclic peptide having the Molecular formula C37 H60 N14 014 S2; a MW of 989.1; and the CAS Registry #: 2580154-02-3. It has all natural amino acids and can also be represented as follows: Ac-Cys-Arg-Gly-Asp-Lys-Gly-Pro-Asp-Cys-NH2 (Cys & Cys Bridge). It can also br represented as follows: L-cysteinyl-L-arginylglycyl-L-.alpha.-aspartyl-L-lysylglycyl-L-prolyl-L-.alpha.-aspartyl-, cyclic (1.fwdarw.9)-disulfide, with N-terminal amino group blocked by an acetyl group and the C-terminal carbonyl group by a carboxyamide group.

In a particular embodiment, the invention composition corresponds to the iRGD-analog is set forth as the structure in FIG. 2 (CEND-1/iRGD-analog). The invention iRGD-analog differs from the prior art iRGD peptides in the specific moieties used to block the amino and carboxy termini, which has resulted in significant advantages over prior art cyclic iRGD peptides. For example, the invention CEND-1/iRGD-analog (set forth in FIG. 2) has the following Molecular formula C37 H60 N14 014 S2; a MW 989.1; and the recent CAS Registry #: 2580154-02-3. Whereas one prior art iRGD with at least one inferior therapeutic property corresponds to an "academic" iRGD having the Molecular Formula: $C_{35}H_{57}N_{13}O_{14}S_2$; a Molecular Weight of 948.04; and CAS Registry No. 1392278-76-0.

Advantages of the invention iRGD-analog (FIG. 2; C37 H60 N14 O14 S2; MW 989.1), relative to prior art CAS Registry No. 1392278-76-0 cyclic peptide and other known iRGD molecules, while maintaining favorable in vitro/in vivo potency and/or efficacy, include one or more of the following:

Favorable pharmacokinetic properties;
Improved stability in plasma/serum;
Improved stability in formulated solution;
Improved stability in storage; and/or
Improved protection from proteases such as aminopeptidases and carboxypeptidases.

In certain embodiments, favorable and/or improved pharmacokinetic properties are selected from one or more of absorption, distribution, metabolism, and/or excretion.

As used herein, the phrase "while maintaining favorable in vitro/in vivo potency and/or efficacy" refers to the continued affect of CEND-1 on the respective therapeutic agents, such that the efficacy and/or potency is not diminished by CEND-1.

Also provided herein is a kit or composition comprising an iRGD-analog (CEND-1); and an anti-cancer agent including, wherein the iRGD-analog is set forth as the structure in FIG. 2.

Examples

Example 1: Phase I Trial (Referred to as CEND-001 Trial) of CEND-1 in Combination with Gemcitabine and Nab-Paclitaxel in Patients with Metastatic Pancreatic Cancer This example demonstrates that CEND-1 was well tolerated in combination with gemcitabine and nab-paclitaxel and provided clinical benefit in patients with advanced pancreatic cancer. When compared to benchmark trials, the response rates are more than doubled. CEND-1 is also referred to herein as the iRGD-analog or CEND-1/iRGD-analogFfigue1 corresponding to the chemical structure set forth in FIG. 2 and CAS Registry #2580154-02-3.

Materials:

CEND-1 drug product is a synthetic peptide manufactured using solid phase peptide synthetic techniques with high chemical purity. CEND-1 for Injection is a sterile, white, lyophilized powder supplied as 100 mg per vial of active ingredient dose strength for intravenous administration. CEND-1 Injection consists of CEND-1 drug substance with sodium acetate trihydrate and mannitol as excipients.

Methods:

The open-label, dose escalation, multicenter (3 active sites in Australia) trial involved a run-in phase with ascending doses of CEND-1 monotherapy (1-7 days), followed by the combination of CEND-1 with nab-paclitaxel (125 $mg/m^2$) and gemcitabine (1000 $mg/m^2$) on days 1, 8, 15 of a 21-day treatment cycle. Patients will first receive the intravenous infusion of nabpaclitaxel (125 $mg/m^2$ over 30 minutes (+3 minutes)). CEND-1 is given intravenously at the applicable dose level as a slow IV push over 1 minute (+30 seconds) immediately following completion of the post-nabpaclitaxel saline flush. The intravenous infusion of gemcitabine (1000 $mg/m^2$ over 30 minutes (+3 minutes)) will be started as soon as possible, but at the latest within 10 minutes of CEND-1 administration.

Safety/Dose Escalation (Cohort 1a)

| Dose Level | Run-in (7 days) | Treatment (28-day cycle) |
|---|---|---|
| 1 | CEND-1 | nabpaclitaxel 125 $mg/m^2$ |
| (1-6 pts) | 0.2 mg/kg | CEND-1 0.2 mg/kg |
| | | gemcitabine 1000 $mg/m^2$ |
| 2 | CEND-1 | nabpaclitaxel 125 $mg/m^2$ |
| (1-6 pts) | 0.8 mg/kg | CEND-1 0.8 mg/kg |
| | | gemcitabine 1000 $mg/m^2$ |
| 3 | CEND-1 | nabpaclitaxel 125 $mg/m^2$ |
| (3-6 pts) | 1.6 mg/kg | CEND-1 1.6 mg/kg |
| | | gemcitabine 1000 $mg/m^2$ |
| 4 | CEND-1 | nabpaclitaxel 125 $mg/m^2$ |
| (3-6 pts) | 3.2 mg/kg | CEND-1 3.2 mg/kg |
| | | gemcitabine 1000 $mg/m^2$ |

Patients (n=31) who had measurable metastatic pancreatic cancer, no prior treatments for metastatic disease and an ECOG PS of 0 to 1 were included. Primary endpoints are safety and optimal biologic dose, secondary and exploratory endpoints included response rates, pharmacokinetics and biomarkers.

Results:

29 patients completed the first treatment cycle and were evaluable for response (data cutoff, 27 Apr. 2020). No dose limiting toxicities were observed. AEs were generally consistent with those of nabpaclitaxel and gemcitabine. The only drug related grade (gr) 3-4 adverse events (AEs) present in >3 patients were neutropenia in 18 (62%) and anemia in 5 (17%) patients. By investigator assessed RECIST 1.1 criteria, 1 pt had a complete response (3.4%), 16 pt. with partial response (55%), 10 pt. with stable disease (34%), and 2 pt. with progressive disease (6.9%). Among the patients with elevated CA19-9 with a postbaseline assessment available, A total of 96% of the patients had a decrease from baseline of at least 20%, and 74% had a decrease of at least 90% and/or had the CA19-9 levels normalized to baseline.

Conclusions:

Administration of CEND-1 in combination with nab-paclitaxel and gemcitabine is safe, with no dose-limiting toxicities. The incidence of Grade 3 and 4 Adverse Event is lower than in similar published trials. The median duration of treatment was longer and the response rates were >2 times higher than in the benchmark trials.

BASELINE SUBJECT CHARACTERISTICS

| | |
|---|---|
| Age | |
| Median | 62 |
| Min-Max | 42-80 |
| Distribution - no. (%) | |
| <65 yr | 15 |
| ≥65 yr | 14 |
| Sex - no. (%) | |
| Female | 11 |
| Male | 18 |
| Race or ethnic group - no.(%) | |
| Asian | 2 |
| White | 25 |
| Other | 2 |
| ECOG Performance Score | |
| 0 | 10 |
| 1 | 19 |

Frequencies below are compared with IMPACT3 trial, data in parenthesis (Von Hoff et al., 2013).

Efficacy Results—Response Rates

The overall response rate (ORR) for all evaluable patients (N=29) was 55% (vs. 23%). The overall disease control rate for 16 weeks was 76% (vs. 48%).

FIG. 1 corresponds to a waterfall plot of maximum percentage changes from baseline in the size of target lesions according to the Response Evaluation Criteria In Solid Tumors 1.1. A total of 16 patients exhibited partial response (55%) and 10 patients had stable disease (34%).

CA19-9

A total of 24 patients had an elevated baseline CA19-9 (≥37 U/L). Of these, 23 patients had at least one on-treatment CA19-9 measurement. A total of 96% of the patients had a decrease from baseline of at least 20% (vs. 61%), and 74% had a decrease of at least 90% and/or had the CA19-9 levels normalized to baseline.

Treatment Exposure

The median duration of treatment was 6.9+ months (vs. 3.9 months), with 76% receiving treatment for at least 6 months (vs. 32%). 86% of the patients had reductions in the nab-paclitaxel dose (vs. 41%) and 76% had reductions in the gemcitabine dose (vs. 47%). In total, 53% of all nab-paclitaxel doses administered during the study were at the full dose of 125 mg per square meter (vs. 71%). The median relative dose intensity (the proportion of the administered cumulative dose relative to the planned cumulative dose) in the nab-paclitaxel-gemcitabine group was 78% for nab-paclitaxel and 82% for gemcitabine (vs 81% and 75%, respectively).

Safety

Table 2 below shows frequencies of bone marrow toxicity observed according to the National Cancer Institute Common Terminology Criteria for Adverse Events (CTCAE), version 5. The frequency of grade 3-4 bone marrow toxicity in this material was 66% for neutropenia, 14% for leukopenia, 23% for neutropenia, 3% for thrombocytopenia and 24% for anaemia. The data from the IMPACT3 [Von Hoff et al. 2013] phase III trial are shown on the middle column for comparison.

TABLE 2

| | no./total no. (%) | |
|---|---|---|
| | nab-Paclitaxel plus Gemcitabine (N = 421) | CEND-1 plus nab-Paclitaxel plus Gemcitabine (N = 29) |
| Grade ≥3 hematologic adverse event | | |
| Neutropenia | 153/405 (38) | 19/29 (66) |
| Leukopenia | 124/405 (31) | 4/29 (14) |
| Thrombocytopenia | 52/405 (13) | 1/29 (3) |
| Anemia | 53/405 (13) | 7/29 (24) |
| Grade ≥3 nonhematologic adverse event occurring in >5% of patients | | |
| Fatigue | 70 (17) | 1/29 (3) |
| Peripheral neuropathy/Median time to onset | 70 (17)/140 days | 4/29 (14)/215 days |
| Diarrhea | 24 (6) | 1/29 (3) |

CEND1-001 Study

In the CEND1-001 trial, as set forth above, CEND-1 was given initially at escalating doses from 0.2 mg/kg to 3.2 mg/kg during a run-in period of 1 to 7 days, during which PK and safety of the single agent were assessed.

There were 8 patients in Cohort 1a: 1 patient at dose level 1 (CEND-1 0.2 mg/kg), 1 patient at dose level 2 (0.8 mg/kg), 3 patients at dose level 3 (1.6 mg/kg) and 3 patients at dose level 4 (3.2 mg/kg). There were 23 patients in Cohort 1b, 11 patients at dose level 3 (1.6 mg/kg), 11 patients at dose level 4 (3.2 mg/kg), and 1 patient who was assigned to dose level 4 (3.2 mg/kg) but withdrew from the study following the run-in period and only received the run-in dosing with CEND-1 0.2 mg/kg.

Of the 31 patients enrolled, 29 were evaluated for efficacy, 31 were evaluated for PK and 30 were evaluated for PD (N=14 at the 1.6 mg/kg CEND-1 dose and N=14 at the 3.2 mg/kg CEND-1 dose level, not including the 2 patients in the CEND-1 low dose group). There were 10 patient deaths reported during the study, 9 caused by progression of primary disease (metastatic pancreatic cancer) and 1 due to a left middle cerebral artery stroke.

Confirmed objective responses (OR) occurred in 17/29 (58.6%) patients (95% CI =38.9, 76.5). The objective response rates for patients treated with CEND-1 1.6 mg/kg and 3.2 mg/kg were 50% (7/14) and 61.5% (8/13) (61.5%), respectively. Disease control was defined as CR+PR+SD>16 weeks and the disease control rate (DCR) was 64.3% (9/14) in the CEND-1 1.6 mg/kg group and 92.3% (12/13) in the CEND-1 3.2 mg/kg group. Overall, the number of patients with progression was 16/29 (55.2%) and the median time to progression was approximately 9.7 months.

These response rates (OR) are clearly above and a marked improvement over what has been achieved in comparable trials historically, Table 3. In the Phase 3 registration trial for nab-paclitaxel, the response rate in first-line metastatic pancreatic cancer patients treated with the gemcitabine/nab-paclitaxel combo was 23% and the PFS 5.5 months (Von Hoff et al., 2013).

TABLE 3

Outcomes of Gemcitabine and Nab-Paclitaxel in Metastatic Pancreatic Cancer Gemcitabine and Nab-Paclitaxel Arm

| Study | Stage | Investigational Agent | Phase | N (Placebo) | ORR (%) | mOS (months) | mPFS (months) | PFS 6 m (%) | PFS 1 Y (%) |
|---|---|---|---|---|---|---|---|---|---|
| VonHoff 2013-International | IV | Gem vs Gem/NP | 3 | 432 | 23 | 8.5 | 5.5 | 45* | 17* |
| Renouf 2020-Canada | IV | Durvalumab and Tremelimumab | 2 | 61 | 23 | 8.8 | 5.4 | 40* | 18* |
| Van Custem 2020-International | IV | PEGPH20 | 2 | 165 | 36 | 11.5 | 7.1 | 52* | 23* |
| Hu 2019-USA | IV | Tarextumab | 2 | 88 | 31.8 | 7.9 | 5.5 | 38* | 11* |
| Karasic 2019-USA | III/IV | Hydroxychloroquine | 2 | 57 | 21.1 | 12.1 | 6.4 | 15* | 50** |
| Tempero 2019-International | IV | Ibrutinib | 3 | 213 | 42 | 10.8 | 6.0 | 50* | 19* |

Because of the trend for an improved outcome with the 3.2 mg/kg dose level, this was chosen as the dose for further exploration in future studies.

Tumor Biomarkers

The number of patients with a ≥50% reduction in CA19-9 from Baseline increased to a high of 20/22 (90.9%) patients at Cycle 5 Day 1.

Tumor biomarker results of CEND-1 at the dose levels of 1.6 mg/kg and 3.2 mg/kg show a trend of decreasing CA values over successive cycles of dosing. This supports the further development of CEND-1, in combination with drugs such as Nab-paclitaxel and Gemcitabine, in patients with metastatic cancers.

CEND-1 Pharmacokinetics

Overall, the median Tmax for CEND-1 was 0.067 hours over all days of PK sampling (minimum was 0.03, maximum 0.55). There was dose proportional increase in Cmax without increase with repeat dosing.

Assessment of plasma CEND-1 parameters demonstrated that exposure (AUC0–t, AUC0–6 h and AUC0–inf) followed the same pattern described for Cmax with a trend to increase with increased dose. Dose normalized PK parameters (AUC0-t/D, AUC0-6 h/D and AUC0-inf/D) were similar between visits and doses.

CEND-1 was eliminated with median T½ values between 1.6 hours and 1.8 hours over all days of PK sampling. CL mean values were between 106.8 mL/h/kg and 266.5 mL/h/kg. The terminal volume of distribution (Vz) mean values were between 220.9 mL/kg and 277.4 mL/kg over all days of PK sampling CEND-1 Safety During the CEND-1 run-in during dose escalation, the following definition of DLT was used:

CEND-1 monotherapy:

A DLT in the run-in period was defined as:

- Grade 4 neutropenia lasting ≥5 days or Grade 3 or 4 neutropenia with fever and/or infection
- Grade 4 thrombocytopenia (or Grade 3 with bleeding)
- Grade 3 or 4 treatment-related non-hematological toxicity (Grade 3 nausea, vomiting or diarrhea that last >72 hours despite maximal treatment constitutes a DLT, insufficient treatment will not constitute an exception to the DLT criteria, as this would constitute inadequate conduct of the study)
- Dosing delay greater than 2 weeks due to treatment-emergent AEs or related severe laboratory abnormalities.

There were no DLTs or grade 3 or 4 adverse events at any CEND-1 dose level during the single agent run-in portion of the study and no clinically significant adverse events attributable to CEND-1 were reported.

During the combination portion of the study, the following definition of dose-limiting toxicity was used:

- Any side effect that is more severe, longer in duration or more frequent than side effects expected from the nab-paclitaxel and gemcitabine package insert.
- Any side effect that is not included in the nab-paclitaxel and gemcitabine package insert that meets the DLT definition of the monotherapy above.

There were no DLTs reported during the study. The majority of TEAEs were CTCAE grade 1 or 2. The number of reported TEAEs at each grade was similar between CEND-1 dose levels. Overall, the severity of TEAEs did not increase with CEND-1 dose. The most common CTCAE grade 3-4 TEAEs by SOC were blood and lymphatic system disorders. Overall, 22 (71.0%) patients reported SAEs. There was no trend of increasing frequency of SAEs with increasing CEND-1 dose. The most common SAEs by SOC were infections and infestations. The safety data for CEND-1 suggest a favorable benefit-risk profile and safety profile. The absence of any CEND-1 monotherapy related SAEs and low frequency of CEND-1 combination therapy related SAEs supports the continued evaluation of this investigational therapy for metastatic exocrine pancreatic cancer.

The invention claimed is:

1. A method for treating, inhibiting, or reducing the volume of a tumor of a pancreatic cancer in a subject or patient in need thereof, wherein the method comprises administering a cyclic peptide corresponding to the chemical structure:

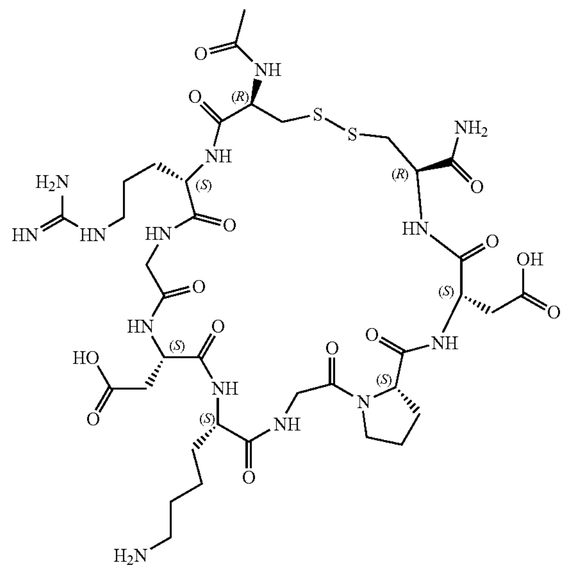

or the pharmaceutically acceptable salt thereof, in a combination with simultaneous, separate or sequential administration of anti-cancer therapy corresponding to gemcitabine and nab-paclitaxel, or pharmaceutically acceptable salts thereof; wherein the cyclic peptide is administered in a range of 0.2-3.2 mg/kg body weight/day or per dose of chemotherapy, nab-paclitaxel is administered in a range of 120-130 mg/m2, and gemcitabine is administered in a range of 900-1100 mg/m2.

2. The method of claim 1, wherein the pancreatic cancer is selected from the group consisting of: primary pancreatic cancer, metastatic pancreatic cancer, refractory pancreatic cancer, cancer drug resistant pancreatic cancer and adenocarcinoma.

3. The method of claim 1, wherein the pancreatic cancer is ductal adenocarcinoma (Stage 0-IV).

4. The method of claim 1, wherein the cyclic peptide is administered before or during the administration of anti-cancer therapy, wherein the anti-cancer therapy is at a dosing regimen selected from the group consisting of: 4 times/day, 3 times/day, twice daily, once daily, once every other day, once every 2$^{nd}$ day, once every 3$^{rd}$ day, once every 4$^{th}$ day, once every 5$^{th}$ day, once every 6$^{th}$ day, once weekly, once every 8$^{th}$ day, once every 9$^{th}$ day, once every 10$^{th}$ day, once every 11$^{th}$ day, once every 12$^{th}$ day, once every 13$^{th}$ day, once every 2 weeks, once every 3 weeks, and/or once per month.

5. The method of claim 1, wherein the cyclic peptide is in a dry formulation or suspended in a biocompatible medium.

6. The method of claim 5, wherein the biocompatible medium is selected from the group consisting of: water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, and lipid-containing emulsions.

7. The method of claim 1, wherein the cyclic peptide is administered intravenously.

8. The method of claim 1, wherein the cyclic peptide is administered in a range of 0.2-3.2 mg/kg body weight/day or per dose of chemotherapy; nab-paclitaxel is administered at 125 mg/m2; and gemcitabine is administered at 1000 mg/m2.

9. The method of claim 1, wherein efficacy or clinical activity of the method is measured by determining: Overall Response Rate (ORR), Progression Free Survival (PFS) and/or Overall Survival (OS).

10. The method of claim 1, wherein efficacy or clinical activity of the method is measured by determining an Overall Response Rate (ORR) of greater than 50%.

11. The method of claim 1, wherein the cyclic peptide is administered in an amount corresponding to 3.2 mg/kg body weight/per dose of anti-cancer therapy.

12. The method of claim 8, wherein the cyclic peptide is administered in an amount corresponding to 3.2 mg/kg body weight/per dose of anti-cancer therapy.

13. A method for treating, inhibiting, or reducing the volume of a tumor of a pancreatic cancer in a subject or patient in need thereof, wherein the method comprises administering a cyclic peptide corresponding to the chemical structure:

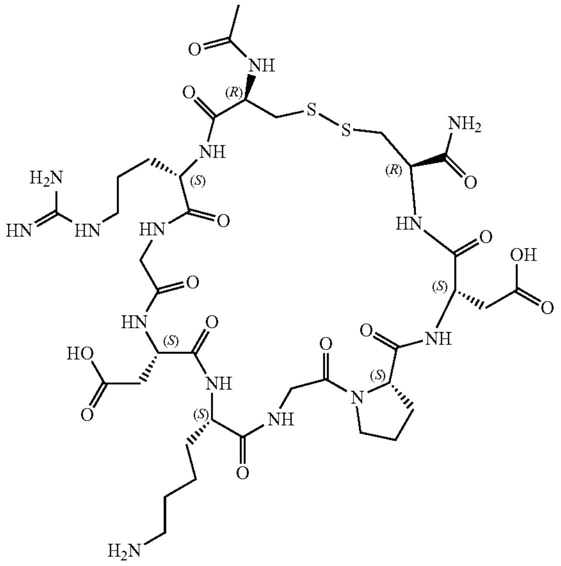

or the pharmaceutically acceptable salt thereof, in a combination with simultaneous, separate or sequential administration of anti-cancer therapy corresponding to gemcitabine and nab-paclitaxel, or pharmaceutically acceptable salts thereof; wherein the cyclic peptide is administered in a range of 0.2-3.2 mg/kg body weight/day or per dose of chemotherapy, nab-paclitaxel is administered in a range of 120-130 mg/m2, and gemcitabine is administered in a range of 900-1100 mg/m2, wherein Progression Free Survival (PFS) is 9.7 months or greater.

14. A method for treating, inhibiting, or reducing the volume of a tumor of a pancreatic cancer in a subject or patient in need thereof, wherein the method comprises administering a cyclic peptide corresponding to the chemical structure:

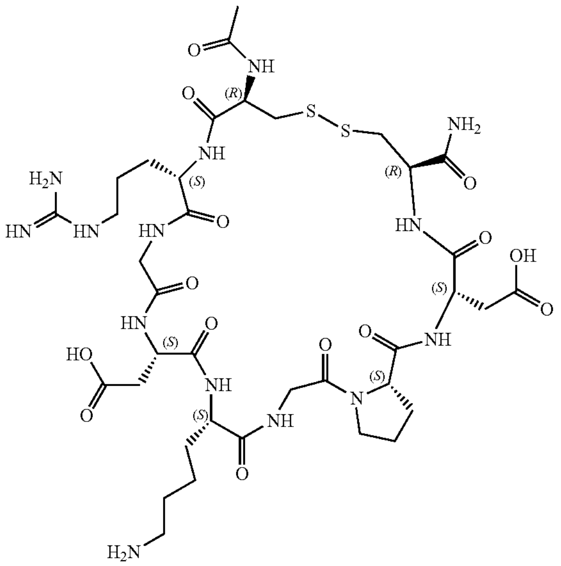

or the pharmaceutically acceptable salt thereof, in a combination with simultaneous, separate or sequential administration of anti-cancer therapy corresponding to gemcitabine and nab-paclitaxel, or pharmaceutically acceptable salts thereof; wherein the cyclic peptide is administered in a range of 0.2-3.2 mg/kg body weight/day or per dose of chemotherapy, nab-paclitaxel is administered in a range of 120-130 mg/m2, and gemcitabine is administered in a range of 900-1100 mg/m2, wherein Overall Survival (OS) is 13.2 months or greater.

* * * * *